US00PP16469P3

(12) United States Plant Patent
Miles

(10) Patent No.: US PP16,469 P3
(45) Date of Patent: Apr. 25, 2006

(54) PEACH TREE NAMED 'V75024'

(50) Latin Name: *Prunus persica*
Varietal Denomination: V75024

(76) Inventor: Neil Miles, RR3, 1683 Gregory Road, St. Catharines, Ontario (CA), L2R 6P9

( * ) Notice: Subject to any disclaimer, the term of this patent is extended or adjusted under 35 U.S.C. 154(b) by 0 days.

(21) Appl. No.: 10/043,572

(22) Filed: Jan. 10, 2002

(65) Prior Publication Data

US 2002/0104135 P1 Aug. 1, 2002

(30) Foreign Application Priority Data

Jan. 29, 2001 (CA) ..... 01-2531

(51) Int. Cl.
*A01H 5/00* (2006.01)

(52) U.S. Cl. ..... Plt./197

(58) Field of Classification Search ..... Plt./197
See application file for complete search history.

(56) References Cited

U.S. PATENT DOCUMENTS

PP12,391 P2 * 2/2002 Zaiger et al. ..... Plt./198
PP13,175 P2 * 11/2002 Howard ..... Plt./195

* cited by examiner

*Primary Examiner*—Bruce R. Campell
*Assistant Examiner*—S. B. McCormick-Ewoldt
(74) *Attorney, Agent, or Firm*—Flynn, Thiel, Boutell & Tanis, P.C.

(57) ABSTRACT

A new and distinct variety of peach tree, which has been given the designation 'V75024', is a high quality mid-to-late season non-melting fleshed clingstone peach that produces high quality mid-to late season fruit suitable for processing as a canned or frozen product.

4 Drawing Sheets

BACKGROUND OF THE VARIETY

Peach cultivar 'V75024' originated at the Horticultural Research Institute of Ontario (now the Department of Plant Agriculture, University of Guelph) at Vineland Station, Ontario, Canada. It arose as a single selection from the seedling population that was derived from a controlled cross of 'Suncling' (patent status unknown) and 'New Jersey Cling 81' (patent status unknown) made in 1975. A large group of these first generation trees were planted and maintained on their own root system, during which time one seedling, which was the present variety, exhibited the outstanding desirable fruit characteristics described below and was selected in 1981.

The peach cultivar 'V75024' was asexually propagated since 1981 by budding on peach seedling rootstock in the research nursery at Vineland Station, Vineland, Ontario, Canada. Comparative records of performance of 'V75024' have been kept on its performance at this site since that date. The asexual propagation demonstrates that such reproduction of the characteristics of the tree are consistent and are established or transmitted through succeeding generations.

SUMMARY OF THE NEW VARIETY

The new and distinct peach 'V75024' is a non-melting fleshed clingstone processing variety. The 'V75024' is self-pollinating and self-fruitful. It is a mid- to late-season maturing peach that produces high quality non-melting fleshed clingstone fruit suitable for processing as a canned or frozen product. It ripens 2 to 5 days later than 'Babygold 5' (patent status unknown), the variety it most closely resembles. Further compared to 'Babygold 5', 'V75024' has slightly shorter and narrower leaves, a flat leafblade profile, has resistance to bacterial spot, and larger fruits. DNA fingerprints of 'V75024' show a characteristic fragment length of 255 using SSR Pchcms2 and characteristic fragment lengths of 143, 142, 141, 140, 139, 138, and 136 using SSR UDP96-013 that are absent in 'Babygold 5'.

The claimed variety differs from its parent, 'Suncling', in that: (1) Its ground skin color is cream-yellow (RHS 10) with dark red punctuation (RHS 480) coloring on approximately 75% of the fruit surface, whereas the skin color of 'Suncling' is golden with some blush when exposed to sun. (2) The stone of the claimed variety is a semi-freestone whereas the stone of 'Suncling' is a non-melting cling stone.

DRAWING

The accompanying photographic illustrations show typical specimens of the fruit and a set of DNA fingerprint profiles of the present new peach variety. The plants were grown in Vineland, Ontario.

Figure 1:
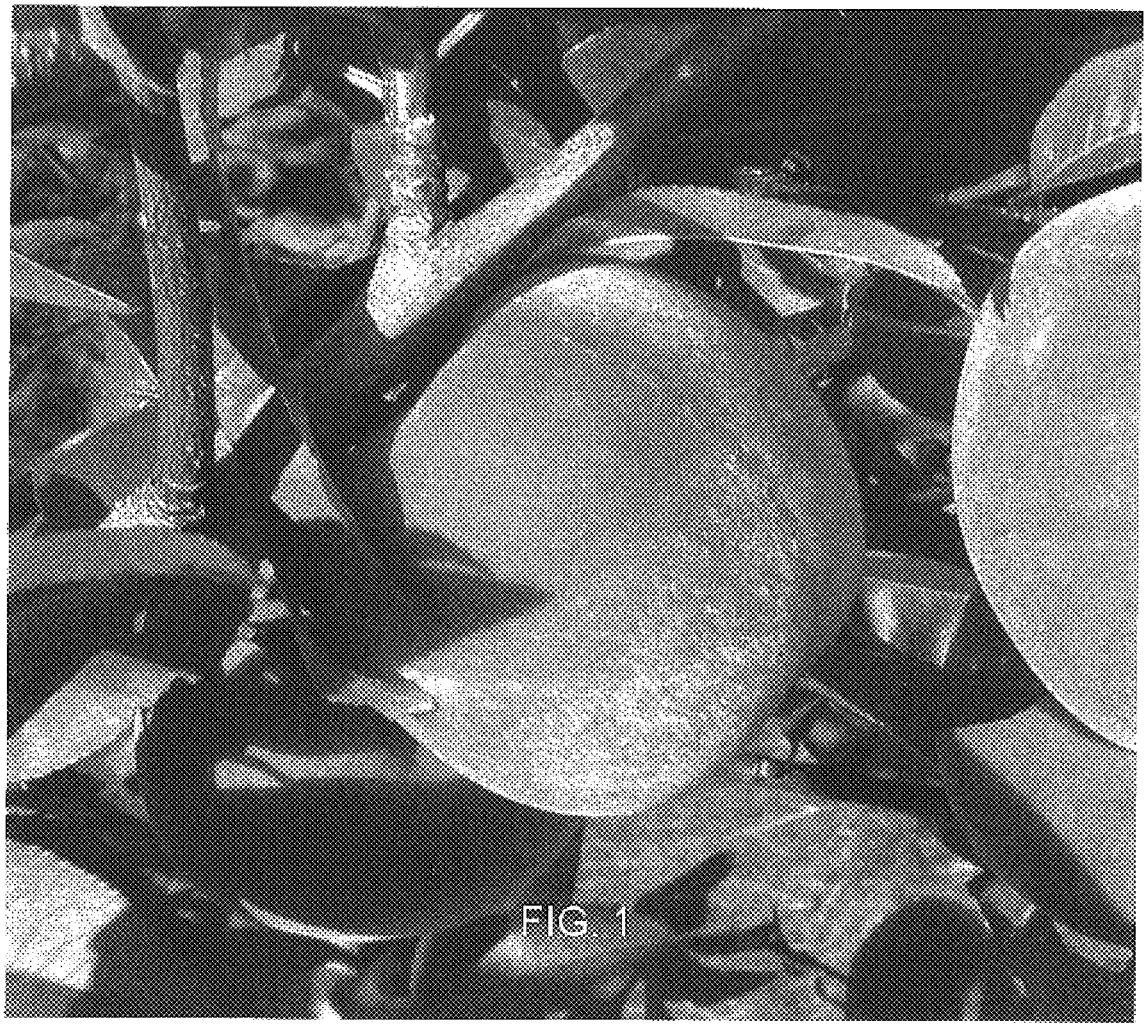

FIG. 1. The illustration shows shoes the fruit of 'V75024' on the tree.

Figure 2:
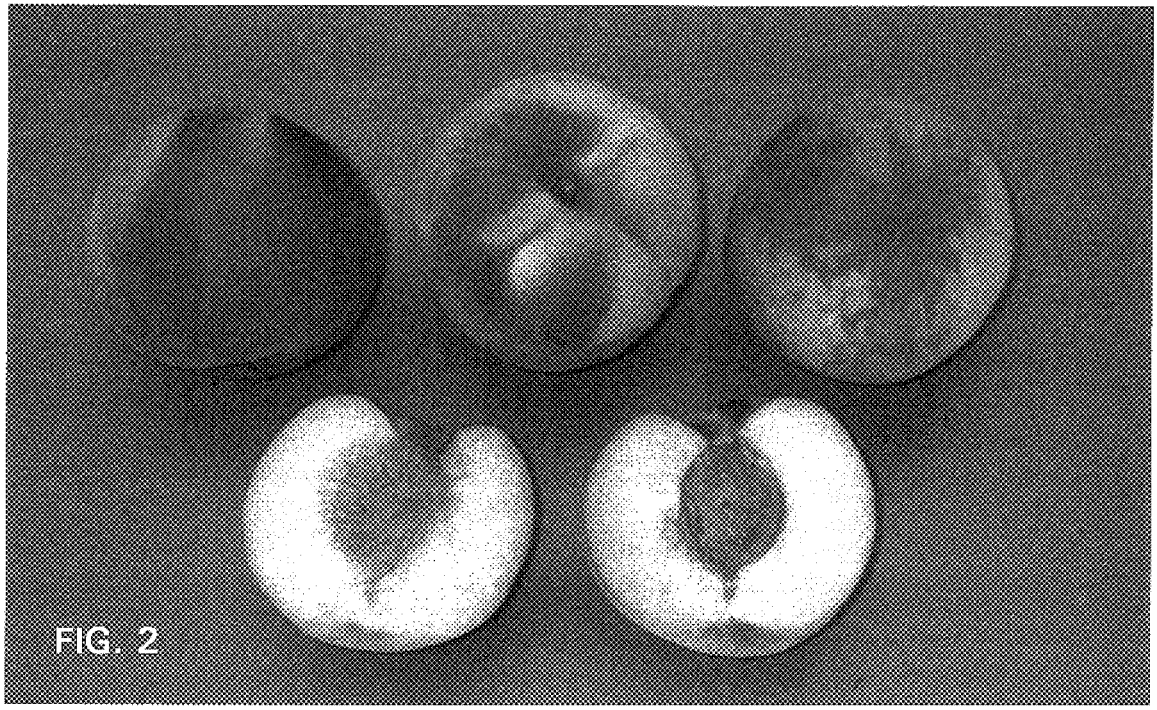

FIG. 2. The illustration shows an exterior and sectional view of a fruit divided in its suture plane to show flesh colour, pit cavity, and the stone remaining in place. The photographic illustration of the fruit was taken shortly after being picked and the colors are as true as is reasonably possible in a colour representation of this variety.

Figure 3:
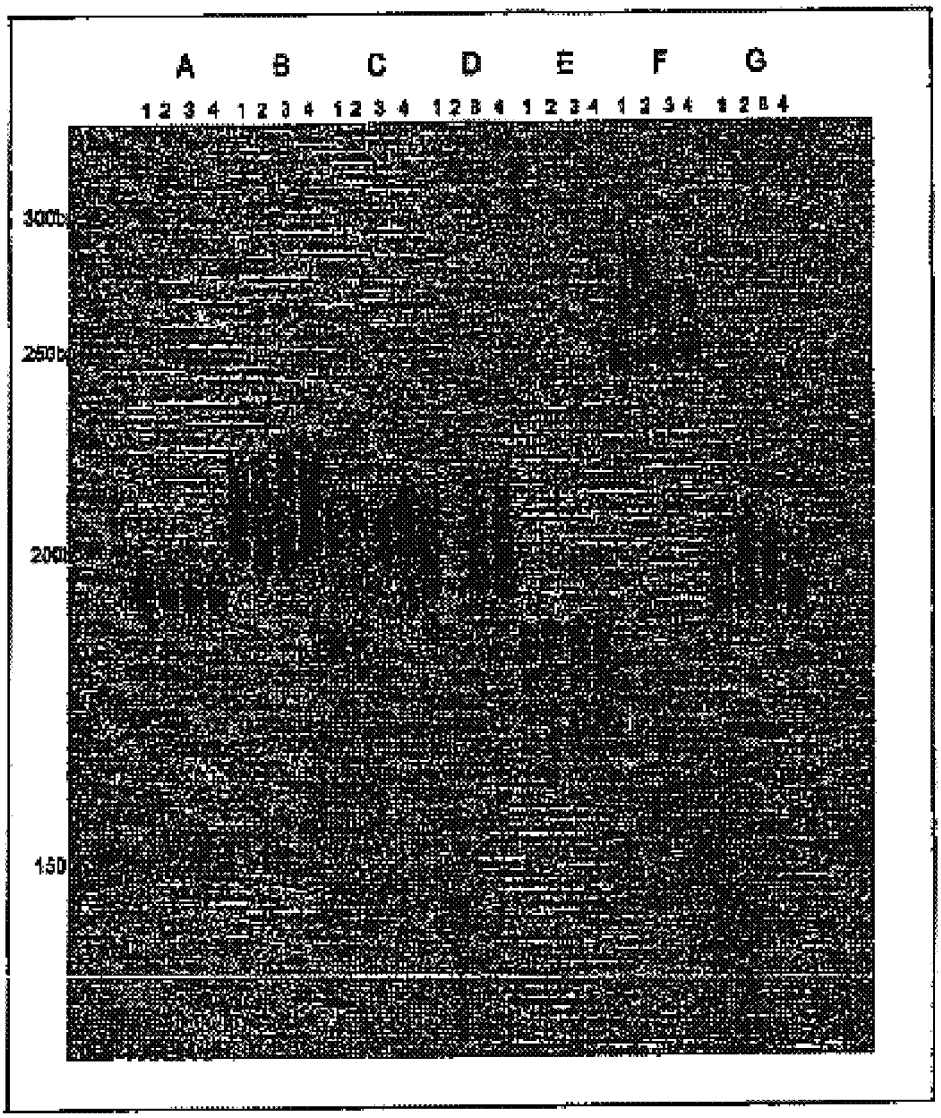

FIG. 3. Is a photograph of a gel with a series of five SSR DNA markers for 'V75024' compared to varieties 'Babygold 5', 'Babygold 7' and 'Catherina'.

Figure 4:
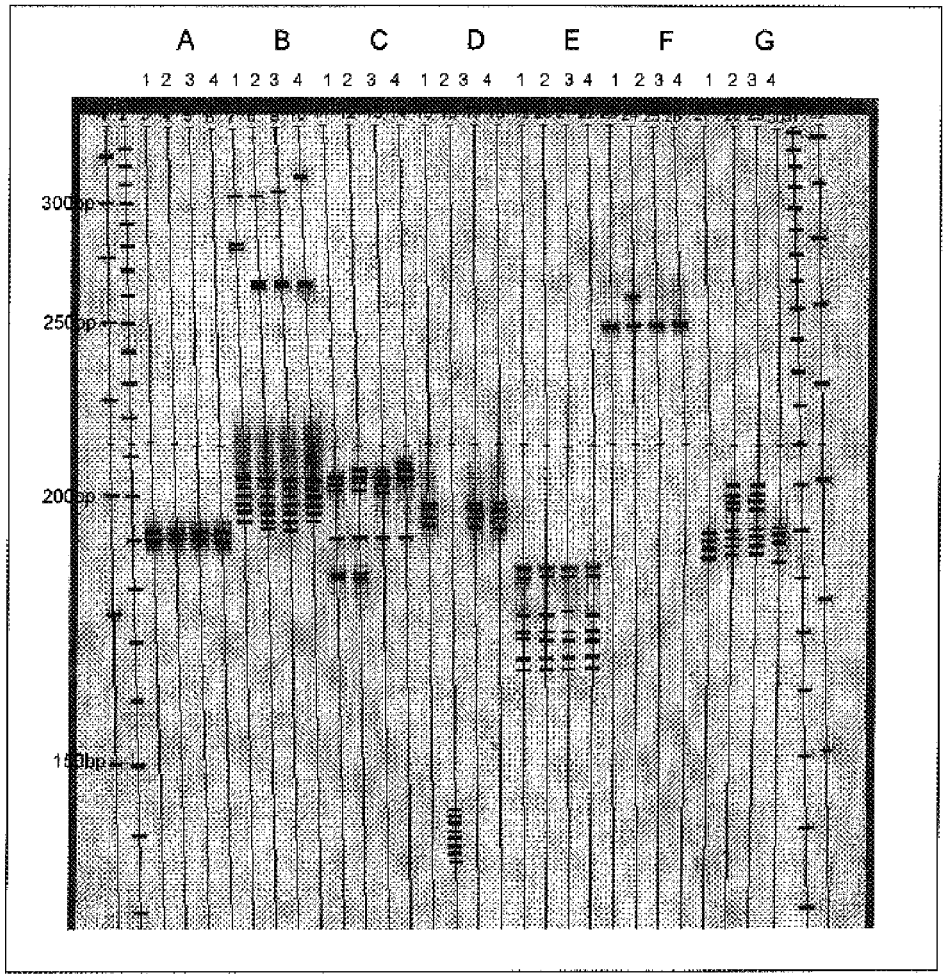

FIG. 4. Is a an overlay of the gel depicted in FIG. 3 with the bands detected by gel analysis.

DETAILED DESCRIPTION

The following detailed description of the new cultivar was obtained through the observation of plants growing at Vineland, Ontario. The observed plants were approximately 14 years of age, and were grown under typical soil and weather conditions for the area. Tree spacing was 12 feet within and 20 feet between rows. Color designations are with reference to The Royal Horticultural Society Color Chart. Common color terms are to be accorded their customary dictionary significance.

Botanical classification: *Prunus persica*, cv 'V75024'.

Tree:

*Size.*—Generally comparable to the 'Babygold 5' cultivar depending on the nature of rootstock, shaping and pruning. For instance a 14 year old tree with commercial pruning when grown at a spacing of 12×20 feet will exhibit a height of approximately 12 to 14 feet and a width of approximately 12 to 15 feet.

*Vigor.*—Very vigorous and generally comparable to that of the 'Babygold 5' cultivar; growth of 6 to 7 feet in height the first growing season.

*Growth.*—Semi-erect to horizontal. As the tree matures, weight of fruit tends to spread width of tree. Usually pruned to vase shape.

*Form.*—Round headed when mature.

*Productivity.*—Very good.

*Regularity of bearing.*—Reliably bears a crop each year. No alternate bearing observed.

Trunk:

*Diameter.*—Generally comparable to that of the 'Babygold 5' cultivar. The diameter will vary with age, spacing, and other cultural conditions. At the age of 14 years using a density planting of 12×20 feet, the girth commonly is approximately 12 to 15 inches measured 14 inches above ground. Trunk diameters are larger when the trees are spaced further apart.

*Surface characteristics.*—Semi-rough and generally comparable to that of the 'Babygold 5' cultivar and commonly with approximately 10 to 14 lenticles per square inch.

*Bark color.*—Grey (RHS 188C) in mid-summer, darker grey (RHS 197A) in winter when dormant.

Branches:

*Size.*—Average circumference 7 inches measured 30 inches above ground. Typical for peach trees and depending on the nature of shaping and pruning.

*Surface characteristics.*—Semi-rough and generally comparable to that of the 'Babygold 5' cultivar.

*Color.*—Grey (RHS 188C).

*Lenticels.*—Small to medium in size, commonly approximately 0.13 inch in length, commonly present at a frequency of approximately 10 to 14 per square inch in young bearing branches, and reddish brown [RHS 165C] in colouration.

*Crotch angles.*—Commonly approximately 35 to 45 degrees, and can be modified to approximately 70 to 75 degrees with supports.

Leaves:

*Size.*—Length ranges from 5.1 to 6.3 inches in length averaging 5.5 inch and slightly shorter compared to 'Babygold 5' cultivar averages 6.0 inch in length. Width ranges from 1.3 to 1.9 inch averaging 1.5 inch, and narrower compared that of the 'Babygold 5' cultivar which averages 1.8 inch in width.

*Configuration.*—Lanceolate. The tip acuminate and the base is cuneate. The leaf blade profile is flat in contrast to the upfolded leaves of that of the 'Babygold 5' cultivar. The angle of the leaf blade is acute at the base and at the tip.

*Margins.*—Serrate.

*Surface.*—Upper surface relatively smooth, glabrous. Lower surface relatively smooth, except for small ridges created by midrib and pinnate venation, glabrous.

*Color.*—Green to deep green [RHS 137A] on the upper surface and light green [RHS 137C to 146A] on the under surface.

*Texture.*—Smooth upper surface and light pubescence on the under surface.

*Petioles.*—Medium in length. Usually about 0.4 inch in length and approximately 0.06 inch in thickness. Color light green [RHS 137C]. Grooved longitudinally.

*Glands.*—Located on upper portion of petiole and lower portion of leaf blade. Number: varies from 0 to 3, average 2. Size: very small, average length 0.05 inch. Configuration: reniform. Colour: greenish yellow [RHS 145A to 151A].

*Anthocyanin colouration.*—None observed in mid-summer.

Flower buds:

*Size.*—Commonly approximately 0.25 inch in diameter and approximately 0.25 inch in length.

*Configuration.*—Generally in groups of two or more. Conical, plump, free. Becomes elongated just before opening.

*Pubescence.*—Pubescent.

*Color.*—Burgandy-red (RHS 60D).

*Pedicel.*—Size medium. Average length 0.40 inch. Average width 0.10 inch. Colour light green [RHS 146B to 137C].

Flowers:

*Date of bloom.*—Approximately May 7 to May 15 at Vineland, Ontario and May 10 to May 15 to that of the 'Babygold 5' cultivar. Duration of flowering is short and comparable to that of the 'Babygold 5' cultivar.

*General appearance.*—Rosaceous. Large, showy, light pink blossoms. Average length 1 inch, average diameter 1.75 inch.

*Flower shape.*—Typical of peach trees.

*Petal number.*—Five, alternately positioned with sepals.

*Petal size.*—Approximately 0.75 inch in length and 1.06 inch in width.

*Petal shape.*—Orbicular, narrows a point of attachment. Edge of outer surface varies from smooth to scalloped.

*Petal color.*—Medium-pink (RHS 56-C) with light stripes. Color fades with age of flower.

*Stamens.*—Number per flower 37 to 45, average 40. Average height 0.6 inch. Filament color white [RHS 158C]. Filament length 0.5 inch. Anther colour purple-red [RHS 183C]. Anther exceeds height of stigma approximately 0.05 inch.

*Pollen.*—Present. Self-fertile. Color light yellow to butter yellow [RHS 2D to 4D].

*Pistil.*—Number: Always 1 per flower. Average length 0.7 inch. Colour light grayish yellow [RHS 149D to 150D] fades to nearly white as flower ages. Stigma is located above anthers. Pubescence is present on ovary.

*Pedicel.*—Average length 0.2 inch. Average width 0.1 inch. Colour: light green to yellowish green [RHS 138B].

Fruit:

*Date of maturity.*—Commonly September 6 at Vineland, Ontario and commonly ripens at 2 to 5 days later than the 'Babygold 5' cultivar. Representative dates during 2002 are September 10 for the present cultivar and September 5 for the 'Babygold 5' cultivar at Vineland, Ontario.

*Configuration.*—Rounded. Symmetric along the suture.

*Uniformity.*—Very good.

*Size.*—Commonly approximately 2.5 to 3.0 inches in diameter, and approximately 1.4 to 1.6 inch in thickness. Suture. Very shallow and narrow suture line. The length from the base to the apex commonly is approximately 2.5 to 3 inches.

*Stem cavity.*—Rounded to slightly elongated in suture plane. Average depth 0.3 inch. Average breadth 1 inch.

*Base.*—Flat and rounded.

*Apex.*—Dimpled at tip, comparable to the 'Babygold 5' cultivar.

Fruit stem:

*Length.*—Commonly approximately 0.4 inch.

*Diameter.*—Commonly approximately 0.15 inch, enlarged at point of fruit attachment.

Fruit skin:

*Thickness.*—Typical for a peach, pubescent, tough similar to that of the 'Babygold 5' cultivar, and tenacious to the flesh.

*Color.*—Ground colour of skin is cream-yellow (RHS 1D) with dark red punctuated colouration (RHS 45D) on approximately 75% of the fruit surface. Maximum red colouration occurs when the trees are planted less densely and the fruit is more exposed to the sun.

*Tendency to crack.*—None.

*Pubescence.*—Present. Greater density compared to that of the 'Babygold 5' cultivar.

Fruit flesh:

*Color.*—Orange-yellow (RHS 18A). Slight anthocyanin colouration from pit cavity into flesh around stone. No anthocyanin colouration directly under skin.

*Firmness.*—Firm to very firm.

*Surface of pit cavity.*—Flesh somewhat tight to the pit due to the rough nature of the pit.

*Juice.*—Medium juicy, comparable to the 'Babygold 5' cultivar.

*Aroma.*—Slight.

*Fibres.*—None present.

*Texture.*—Non-melting, comparable to the 'Babygold 5' cultivar.

*Flavour.*—Intermediate acidity, comparable to the 'Babygold 5' cultivar.

*Ripening.*—Substantially even throughout.

*Eating quality.*—Very mild and low acid taste.

Stone:

*Degree of freedom.*—Semi-freestone, the stone has strong adherence to the flesh.

*Fibres.*—None present.

*Size.*—Commonly approximately 0.63 inch in length and approximately 0.88 inch in width.

*Color.*—Red. The colouration darkens upon exposure to air.

*Form.*—Ovoid in shape (in same plane as suture).

*Base.*—Rounded and flat and approximately 0.25 inch in diameter.

*Apex.*—Flat. Average length 0.1 inch.

*Sides.*—Very rough. Vary from equal to unequal. Some stones have one side extending further from suture plane.

*Surface.*—Irregularly furrowed toward apex, pitted toward base. Pits vary from round to elongated. One long furrow on each side of suture, extending from base to apex. Narrow ridges vary in length, with rough surface. Ridges approximately 0.03 to 0.06 inch in depth.

*Tendency to split.*—None.

Cold reaction: The 'V75024' cultivar is medium-hardy to hardy, comparable to the cold hardiness of the 'Babygold 5' cultivar. Winter injury is confined to the previous two season's growth.

Disease resistance:

*Canker* (*Cytospora* spp.).—Moderately resistant, comparable to that of the 'Babygold 5' cultivar.

*Bacterial spot* (*Xanthomonas campestris* pv. *pruni*).—'V75024' cultivar is resistant. The 'Babygold 5' cultivar is susceptible.

Use: Processing suitable for processing as a canned or frozen product.

Keeping quality: Keeps approximately 5 to 8 days at room temperature [when picked at commercial ripening] and has kept in excess of three weeks in cold storage.

Shipping quality: Good. Handles and ships well due to very firm nature.

Although the new 'V75024' cultivar of peach tree possesses the above-described characteristics as a result of the growing conditions at Vineland, Ontario, it is to be expected that variations of the usual type and magnitude may appear that are caused by differences in growing conditions, fertilization, pruning, pest control and other horticultural practices when the new cultivar is grown in different environments.

DNA fingerprints

DNA extraction

Young leaf tissue samples of V75024, Babygold 5, Babygold 7, and Catherina were collected in May and September 2003 from nurseries located near Vineland, Ontario. The tissue was immediately frozen in liquid nitrogen, transported on dry ice and frozen at −80° C. DNA was extracted according to Serrano et al., 2002 with some modifications. Approximately 50 mg of leaf tissue were ground in a Fast Prep machine (QBioGene) with 200 uL extraction buffer (100 mM Tris-HCl, 1.4 M NaCl, 20 mM EDTA, 2% CTAB, 1% PVP, 0.2% β-mercaptoethanol, 0.1% $NaHSO_3$) and incubated at 65° C. for 30 minutes. An equal volume of chloroform:isoamyl alcohol (24:1) was added, mixed by inversion and centrifuged at 6,000×g for 15 minutes. The supernatant was transferred to a new tube, mixed with 10 ug RNAse A and incubated at 37° C. for 30 minutes. An aliquot of 130 uL ice-cold isopropanol was added, mixed by inversion and centrifuged at 13,000×g for 5 minutes to recover the nucleic acid precipitate. The supernatant was removed and the pellet was washed with 400 uL of 10 mM ammonium acetate in 76% ethanol for 10 minutes and dried at room temperature. The pellet was re-suspended overnight at 4° C. in 200 uL of sterile $ddH_2O$ (ph 8.0) and quantified using a Spectramax Plus spectrophotometer (Molecular Devices). The DNA was then stored at −20° C.

PCR amplification

Microsatellite primer pairs previously developed in peach (Table 1) were synthesized by Sigma Genosys (Oakville, ON). PCR was performed in a Robocycler 96 (Stratagene) and consisted of one incubation of 5 minutes at 94° C. followed by 35 cycles of 45 seconds at 94° C., 45 seconds at the appropriate annealing temperature (Table 1) and 1 minute at 72° C. The final cycle was followed by a 5 minute incubation at 72° C. Amplification reactions were carried out in 25 uL volumes containing 10 mM Tris-HCl pH 8.3, 50 mM KCl, 1.5 mM $MgCl_2$, 100 uM of each dNTP, 10 pmol of each primer, 1U Taq polymerase (Sigma) and approximately 200 ng peach genomic DNA. Following amplification, 10 uL of the PCR reaction was separated on a 1% agarose gel containing ethidium bromide to verify PCR amplification. Samples were then stored at −20° C. prior to polyacrylamide gel electrophoresis.

TABLE 1

List of microsatellite markers (SSRs) used to identify peach varieties

| SSR primer pair | Sequence (5'–3') | Sequence ID | Annealing temperature (° C.) | Reference |
|---|---|---|---|---|
| CPPCT030-A | TGAATATTGT-TCCTCAATTC | No. 1 | 50 | Aranzana et al., (2002) |
| CPPCT030-B | CTCTAGGCAA-GAGATGAGA | No. 2 | | |
| Pchcms2-A | AGGGTCGTCT-CTTTGAC | No. 3 | 50 | Sosinski et al., (2000) |
| Pchcms2-B | CTTCGTTTCA-AGGCCTG | No. 4 | | |
| Pchcms5-A | CGCCCATGAC-AAACTTA | No. 5 | 50 | Sosinski et al., (2000) |
| Pchcms5-B | GTCAAGAGGT-ACACCAG | No. 6 | | |
| UDP96-013-A | ATTCTTCACT-ACACGTGCAC-G | No. 7 | 57 | Cipriani et al., (1999), Testolin et al., (2000) |
| UDP96-013-B | CCCCAGACAT-ACTGTGGCTT | No. 8 | | |
| UDP98-407-A | AGCGGCAGGC-TAAATATCAA | No. 9 | 52 | Cipriani et al., (1999), Testolin et al., (2000) |
| UDP98-407-B | AATCGCCGAT-CAAAGCAAC | No. 10 | | |
| BPPCT025-A | TCCTGCGTAG-AAGAAGGTA-GC | No. 11 | 57 | Dirlewanger et al., (2002) |
| BPPCT025-B | CGACATAAAG-TCCAAATGGC | No. 12 | | |
| Pchgms1-A | CGGTAAATAT-GCCCATTGTG-CAATC | No. 13 | 52 | Sosinski et al., (2000) |
| Pchgms1-B | GGATCATTGA-ACTACGTCAA-TCCTC | No. 14 | | |

Visualization of microsatellites

The PCR products were denatured by addition of an equal volume of sample buffer (95% de-ionized formamide, 10 mM NaOH, 0.05% bromophenol blue, 0.05% xylene cyanol). Samples were heated at 94° C. for 6 minutes and immediately placed on ice. Two microliters of each denatured preparation were loaded onto a 38×50 cm 6% polyacrylamide sequencing gel containing 7 M urea in 1× TBE buffer (90 mM Tris, 90 mM boric acid, 1 mM EDTA). Gels were run on a Sequi-Gen GT Nucleic Acid Electrophoresis Cell (Bio-Rad) for 4–5 hours at 85W. Following electrophoresis, gels were silver-stained using the SilverXpress Silver Staining Kit (Invitrogen), scanned on a HP scanjet 5470c scanner and dried on a Slab Gel Dryer SGD2000 (Savant). Fragment sizes were determined with 10-bp and 25-bp ladder DNA sizing markers (Invitrogen) using The Discovery Series, Quantity One software program (Bio-Rad).

Fingerprint Profile

The microsatellite primer pairs revealed genetic differences between and among the four peach varieties (FIGS. 1 and 2). Table 2 summarizes the fragment sizes detected for each of the primer pairs used based on repeated samples. There are a number of fragments that can be used to distinguish each of the four varieties using pairwise or any combination of comparisons. For example, fragments 262/264 from SSR BPPCT025 which are present in V75024, Catherina and Babygold 7 are not detected in Babygold 5. The characteristic fragment sizes that can be used to distinguish V75024 from all three reference varieties are presented in bold type in Table 2. These characteristic fragments are fragment 255 using SSR Pchcms2 and fragments 143, 142, 141, 140, 139, 138, 137, and 136 using SSR UDP96-013. These fragments are produced from DNA extracts of V75024 but are absent in Babygold 5, Babygold 7, and Catherina.

TABLE 2

Fragment sizes (bp) detected for four peach varieties using seven microsatellite primer pairs. Fragment sizes listed in bold are unique fragment sizes detected in V75024 that are not detected in the other three varieties.

| | Peach Variety | | | |
|---|---|---|---|---|
| SSR | V75024 | Babygold 5 | Babygold 7 | Catherina |
| CPPCT030 | 200, 198, 196, 195, 190, 189, 187, 185 | 190, 188, 187, 184 | 191, 190, 188, 184 | 200, 198, 197, 195, 190, 189, 187, 185 |
| Pchcms2 | **255**, 245 | 245 | 246 | 246 |
| Pchcms5 | 183, 181, 174, 171, 169, 166, 164 | 183, 181, 174, 171, 170, 166, 164 | 183, 181, 174, 171, 169, 166, 164 | 183, 181, 174, 171, 169, 166, 164 |
| UDP96-013 | **143, 142, 141, 140, 139, 138, 137, 136** | 197, 196, 194, 192 | 197, 195, 194, 191 | 197, 196, 194, 192 |
| UDP98-407 | 205, 204, 202, 200, 190, 182, 181 | 204, 202, 200, 190, 182, 181 | 207, 205, 203, 190 | 205, 203, 202, 200, 190 |
| BPPCT025 | 304, 265, 263, 204, 202, 200, 198, 196, 194, 193 | 304, 281, 279, 204, 202, 200, 198, 197, 194 | 312, 263, 262, 203, 201, 199, 197, 195, 194 | 305, 264, 262, 204, 202, 200, 198, 196, 194, 192 |
| Pchgms1 | 191, 190 | 192, 190 | 192, 190 | 192, 190 |

FIG. 1. Silver stained 6% polyacrylamide sequencing gel of four peach cultivars (1 = Babygold 5, 2 = V75024, 3 = Catherina, 4 = Babygold 7) using seven microsatellites (A = pchgms1, B = BPPCT025, C = UDP98-407, D = UDP96-013, E = pchcms5, F = pchcms2, G = CPPCT030).

FIG. 2. Silver stained 6% polyacrylamide sequencing gel of four peach cultivars (1 = Babygold 5, 2 = V75024, 3 = Catherina, 4 = Babygold 7) using seven microsatellites (A = pchgms1, B = BPPCT025, C = UDP98-407, D = UDP96-013, E = pchcms5, F = pchcms2, G = CPPCT030) showing banding patterns identified using Quantity One software.

References

Aranzana M.J., Garcia-Mas, J., Carbo, J. and P. Arus. 2002. Development and variability analysis of microsatellite markers in peach. Plant Breeding. 121:87–92.

Cipriani G., Lot G., Huang W-G., Marrazzo M.T., Peterlunger E. and R. Testolin. 1999.

AC/GT and AG/CT microsatellite repeats in peach [*Prunus persica* (L) Batsch]: isolation, characterization and cross-species amplification in *Prunus*. Theor. Appl. Genet. 99:65–72.

Dirlewanger E., Cosson P., Tavaud M., Aranzana M.J., Poizat C., Zanetto A., Arus P. and F. Laigret. 2002. Development of microsatellite markers in peach [*Prunus persica* (L.) Batsch] and their use in genetic diversity analysis in peach and sweet cherry (*Prunus avium* L.). Theor. Appl. Genet. 105:127–138.

Serrano B., Gomez-Aparisi J and J.I. Hormaza. 2002. Molecular fingerprinting of *Prunus* rootstocks using SSRs. J. Hort. Sci. Biotech. 77(3):368–372.

Sosinski B., Gannavarapu M., Hager L.D., Beck L.E., King G.J., Ryder C.D., Rajapakse S., Baird W.V., Ballard R.E. and A.G. Abbott. 2000. Characterization of microsatellite markers in peach [*Prunus persica* (L.) Batsch]. Theor. Appl. Genet. 101:421–428.

Testolin R., Marrazzo T., Cipriani G., Quarta R., Verde I., Dettori M.T., Pancaldi M. and S. Sansavini. 2000. Microsatellite DNA in peach (*Prunus persica* L. Batsch) and its use in fingerprinting and testing the genetic origin of cultivars. Genome. 43:512–520.

SEQUENCE LISTING

```
<160> NUMBER OF SEQ ID NOS: 14

<210> SEQ ID NO 1
<211> LENGTH: 20
<212> TYPE: DNA
<213> ORGANISM: Prunus persica
<300> PUBLICATION INFORMATION:
<301> AUTHORS: Aranzana et al
<302> TITLE: Development and Variability Analysis of
      Microsatellite Markers in Peach
<303> JOURNAL: Plant Breeding
<304> VOLUME: 121
<306> PAGES: 87-92
<307> DATE: 2002

<400> SEQUENCE: 1

tgaatattgt tcctcaattc                                                20


<210> SEQ ID NO 2
<211> LENGTH: 19
<212> TYPE: DNA
<213> ORGANISM: Prunus persica
<300> PUBLICATION INFORMATION:
<301> AUTHORS: Aranzana et al
<302> TITLE: Development and Variability Analysis of
      Microsatellite Markers in Peach
<303> JOURNAL: Plant Breeding
<304> VOLUME: 121
<306> PAGES: 87-92
<307> DATE: 2002

<400> SEQUENCE: 2

ctctaggcaa gagatgaga                                                 19


<210> SEQ ID NO 3
<211> LENGTH: 17
<212> TYPE: DNA
<213> ORGANISM: Prunus persica
<300> PUBLICATION INFORMATION:
<301> AUTHORS: Sosinski et al
<302> TITLE: Characterization of Microsatellite Markers
      in Peach [Prunus persica (L.) Batsch]
<303> JOURNAL: Theor. Appl. Genet.
<304> VOLUME: 101
<306> PAGES: 421-428
<307> DATE: 2000

<400> SEQUENCE: 3

agggtcgtct ctttgac                                                   17


<210> SEQ ID NO 4
<211> LENGTH: 17
<212> TYPE: DNA
<213> ORGANISM: Prunus persica
<300> PUBLICATION INFORMATION:
```

-continued

<301> AUTHORS: Sosinski et al
<302> TITLE: Characterization of Microsatellite Markers
in Peach [Prunus persica (L.) Batsch]
<303> JOURNAL: Theor. Appl. Genet.
<304> VOLUME: 101
<306> PAGES: 421-428
<307> DATE: 2000

<400> SEQUENCE: 4 cttcgtttca aggcctg 17

<210> SEQ ID NO 5
<211> LENGTH: 17
<212> TYPE: DNA
<213> ORGANISM: Prunus persica
<300> PUBLICATION INFORMATION:
<301> AUTHORS: Sosinski et al
<302> TITLE: Characterization of Microsatellite Markers
in Peach [Prunus persica (L.) Batsch]
<303> JOURNAL: Theor. Appl. Genet.
<304> VOLUME: 101
<306> PAGES: 421-428
<307> DATE: 2000

<400> SEQUENCE: 5 cgcccatgac aaactta 17

<210> SEQ ID NO 6
<211> LENGTH: 17
<212> TYPE: DNA
<213> ORGANISM: Prunus persica
<300> PUBLICATION INFORMATION:
<301> AUTHORS: Sosinski et al
<302> TITLE: Characterization of Microsatellite Markers
in Peach [Prunus persica (L.) Batsch]
<303> JOURNAL: Theor. Appl. Genet.
<304> VOLUME: 101
<306> PAGES: 421-428
<307> DATE: 2000

<400> SEQUENCE: 6 gtcaagaggt acaccag 17

<210> SEQ ID NO 7
<211> LENGTH: 21
<212> TYPE: DNA
<213> ORGANISM: Prunus persica
<300> PUBLICATION INFORMATION:
<301> AUTHORS: Cipriani et al
<302> TITLE: AC/GT and AG/CT Microsatellite Repeats in Peach
[Prunus persica (L) Batsch]: isolation. Characterization, and
cross-species.Amplification in Prunus
<303> JOURNAL: Theor. Appl. Genet.
<304> VOLUME: 99
<306> PAGES: 65-72
<307> DATE: 1999
<300> PUBLICATION INFORMATION:
<301> AUTHORS: Testolin et al
<302> TITLE: Microsatellite DNA in Peach
[Prunus persica L. Batsch] and its Use in
Fingerprinting and Testing the Genetic Origin
of Cultivars
<303> JOURNAL: Genome
<304> VOLUME: 43
<306> PAGES: 512-520
<307> DATE: 2000

<400> SEQUENCE: 7 attcttcact acacgtgcac g 21

-continued

<210> SEQ ID NO 8
<211> LENGTH: 20
<212> TYPE: DNA
<213> ORGANISM: Prunus persica
<300> PUBLICATION INFORMATION:
<301> AUTHORS: Cipriani et al
<302> TITLE: AC/GT and AG/CT Microsatellite Repeats in Peach
[Prunus persica (L) Batsch]: isolation. Characterization, and
cross-species.Amplification in Prunus
<303> JOURNAL: Theor. Appl. Genet.
<304> VOLUME: 99
<306> PAGES: 65-72
<307> DATE: 1999
<300> PUBLICATION INFORMATION:
<301> AUTHORS: Testolin et al
<302> TITLE: Microsatellite DNA in Peach
[Prunus persica L. Batsch] and its Use in
Fingerprinting and Testing the Genetic Origin
of Cultivars
<303> JOURNAL: Genome
<304> VOLUME: 43
<306> PAGES: 512-520
<307> DATE: 2000

<400> SEQUENCE: 8 ccccagacat actgtggctt 20

<210> SEQ ID NO 9
<211> LENGTH: 20
<212> TYPE: DNA
<213> ORGANISM: Prunus persica
<300> PUBLICATION INFORMATION:
<301> AUTHORS: Cipriani et al
<302> TITLE: AC/GT and AG/CT Microsatellite Repeats in Peach
[Prunus persica (L) Batsch]: isolation.Characterization, and
cross-species.Amplification in Prunus
<303> JOURNAL: Theor. Appl. Genet.
<304> VOLUME: 99
<306> PAGES: 65-72
<307> DATE: 1999
<300> PUBLICATION INFORMATION:
<301> AUTHORS: Testolin et al
<302> TITLE: Microsatellite DNA in Peach
[Prunus persica L. Batsch] and its Use in
Fingerprinting and Testing the Genetic Origin
of Cultivars
<303> JOURNAL: Genome
<304> VOLUME: 43
<306> PAGES: 512-520
<307> DATE: 2000

<400> SEQUENCE: 9 agcggcaggc taaatatcaa 20

<210> SEQ ID NO 10
<211> LENGTH: 19
<212> TYPE: DNA
<213> ORGANISM: Prunus persica
<300> PUBLICATION INFORMATION:
<301> AUTHORS: Cipriani et al
<302> TITLE: AC/GT and AG/CT Microsatellite Repeats in Peach
[Prunus persica (L) Batsch]: isolation.Characterization, and
cross-species.Amplification in Prunus
<303> JOURNAL: Theor. Appl. Genet.
<304> VOLUME: 99
<306> PAGES: 65-72
<307> DATE: 1999
<300> PUBLICATION INFORMATION:
<301> AUTHORS: Testolin et al
<302> TITLE: Microsatellite DNA in Peach
[Prunus persica L. Batsch] and its Use in
Fingerprinting and Testing the Genetic Origin
of Cultivars
<303> JOURNAL: Genome -continued

<304> VOLUME: 43
<306> PAGES: 512-520
<307> DATE: 2000

<400> SEQUENCE: 10 aatcgccgat caaagcaac 19

<210> SEQ ID NO 11
<211> LENGTH: 21
<212> TYPE: DNA
<213> ORGANISM: Prunus persica
<300> PUBLICATION INFORMATION:
<301> AUTHORS: Dirlewanger et al
<302> TITLE: Development of Microsatellite Markers in Peach
[Prunus persica (L.) Batsch] and Their Use in
Genetic Diversity
Analysis in Peach and Sweet Cherry
<303> JOURNAL: Theor. Appl. Genet.
<304> VOLUME: 105
<306> PAGES: 127-138
<307> DATE: 2002

<400> SEQUENCE: 11 tcctgcgtag aagaaggtag c 21

<210> SEQ ID NO 12
<211> LENGTH: 20
<212> TYPE: DNA
<213> ORGANISM: Prunus persica
<300> PUBLICATION INFORMATION:
<301> AUTHORS: Dirlewanger et al
<302> TITLE: Development of Microsatellite Markers in Peach
[Prunus persica (L.) Batsch] and Their Use in
Genetic Diversity
Analysis in Peach and Sweet Cherry
<303> JOURNAL: Theor. Appl. Genet.
<304> VOLUME: 105
<306> PAGES: 127-138
<307> DATE: 2002

<400> SEQUENCE: 12 cgacataaag tccaaatggc 20

<210> SEQ ID NO 13
<211> LENGTH: 25
<212> TYPE: DNA
<213> ORGANISM: Prunus persica
<300> PUBLICATION INFORMATION:
<301> AUTHORS: Sosinski et al
<302> TITLE: Characterization of Microsatellite Markers
in Peach [Prunus persica (L.) Batsch]
<303> JOURNAL: Theor. Appl. Genet.
<304> VOLUME: 101
<306> PAGES: 421-428
<307> DATE: 2000

<400> SEQUENCE: 13 gggtaaatat gcccattgtg caatc 25

<210> SEQ ID NO 14
<211> LENGTH: 25
<212> TYPE: DNA
<213> ORGANISM: Prunus persica
<300> PUBLICATION INFORMATION:
<301> AUTHORS: Sosinski et al
<302> TITLE: Characterization of Microsatellite Markers
in Peach [Prunus persica (L.) Batsch]
<303> JOURNAL: Theor. Appl. Genet.
<304> VOLUME: 101
<306> PAGES: 421-428

-continued

<307> DATE: 2000

<400> SEQUENCE: 14 ggatcattga actacgtcaa tcctc 25

I claim:

1. A new and distinct peach tree variety substantially as shown and described herein.

* * * * *